United States Patent [19]

Sato

[11] 4,034,945

[45] July 12, 1977

[54] DEVICE FOR SUSPENDING A NURSING BOTTLE

[76] Inventor: Isao Sato, 7-5, 5-chome, Washibetsucho, Noboribetsu, Hokkaido, Japan

[21] Appl. No.: 640,911

[22] Filed: Dec. 15, 1975

[30] Foreign Application Priority Data

Dec. 16, 1974   Japan ............... 49-152915[U]

[51] Int. Cl.² ........................................ A47D 15/00
[52] U.S. Cl. ............................. 248/103; 248/106; 248/296
[58] Field of Search ................. 248/102–106, 248/124, 283, 285, 286, 296

[56]  References Cited

U.S. PATENT DOCUMENTS

| 713,832 | 11/1902 | Bailey | 248/124 |
|---|---|---|---|
| 1,082,808 | 12/1913 | Hubbard | 248/107 X |
| 1,220,266 | 3/1917 | Ott | 248/103 |
| 1,284,010 | 11/1918 | Wilbur | 248/103 |
| 1,554,201 | 9/1925 | Dalzell | 248/103 |
| 1,734,522 | 11/1929 | Kauffman | 248/103 |
| 1,820,420 | 8/1931 | Aerick | 248/103 |
| 2,015,280 | 9/1935 | Morishita | 248/103 X |
| 2,557,570 | 6/1951 | Seiger | 248/106 X |
| 2,909,381 | 10/1959 | Bates | 248/124 X |

FOREIGN PATENT DOCUMENTS 199,288   6/1923   United Kingdom ............ 248/103

Primary Examiner—Lawrence J. Staab
Attorney, Agent, or Firm—Oblon, Fisher, Spivak, McClelland & Maier

[57]  ABSTRACT

Disclosed is a device for suspending an infant's nursing bottle having a support means capable of both horizontal and vertical adjustment as well as permitting a pivoting action about an upright support. Further, easily attachable bottle gripping means permit the positioning of the nursing bottle at an appropriate degree of inclination.

3 Claims, 6 Drawing Figures

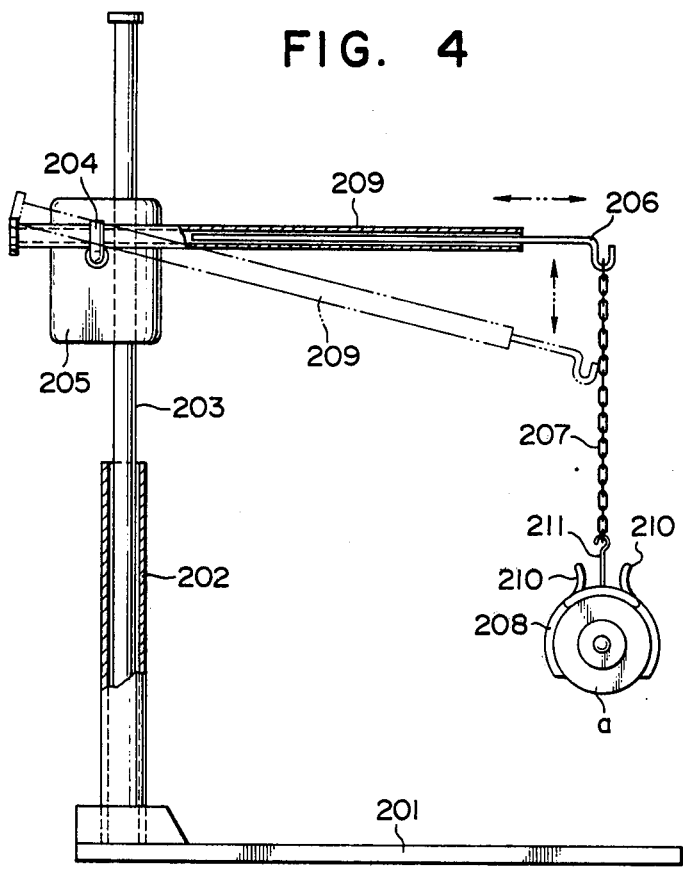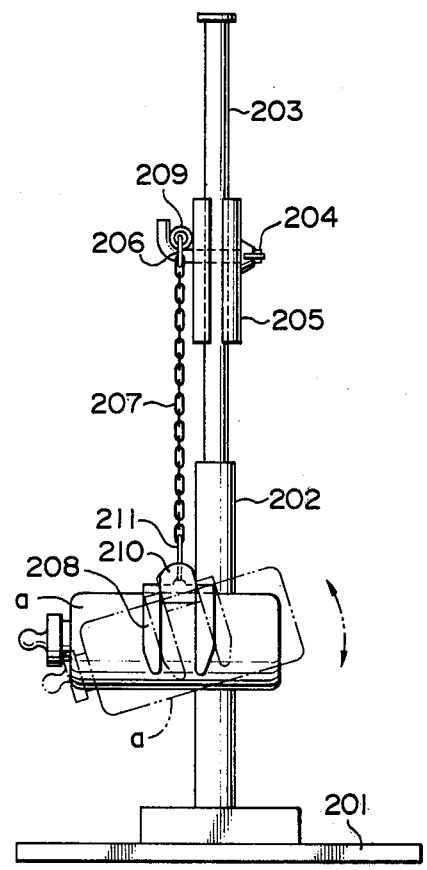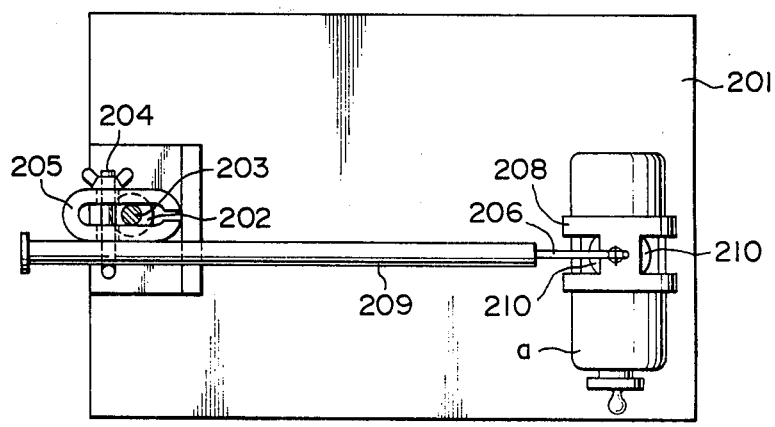

4,034,945

DEVICE FOR SUSPENDING A NURSING BOTTLE

BACKGROUND OF THE INVENTION

Field of the Invention

This invention relates generally to a device for suspending an infant's nursing bottle over a crib, playpen or the like and has a support means permitting both horizontal and vertical adjustment of the bottle, a bottle gripper allowing the bottle to be inclined to an appropriate degree, and a pivot mechanism allowing the bottle suspension means to be pivoted about the adjustable support.

SUMMARY OF THE INVENTION

Among the objects of this invention is to provide a device that permits the suspension of a nursing bottle over a crib, playpen or the like.

Another object of this invention is to provide a device for suspending a nursing bottle that permits the bottle to be adjusted both horizontally and vertically with respect to the surface upon which the infant is lying.

A still further object of this invention is to provide a device for suspending a nursing bottle permitting the bottle to be inclined to the appropriate degree to ensure that the infant may consume all of the liquid within the bottle.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4 is a side view of another embodiment of the device for suspending a nursing bottle, with portions shown in cross-section.

FIG. 5 is an end view of the device of FIG. 4.

FIG. 6 is a top view of the device shown in FIG. 4.

DESCRIPTION OF A PREFERRED EMBODIMENT

Figure 1:
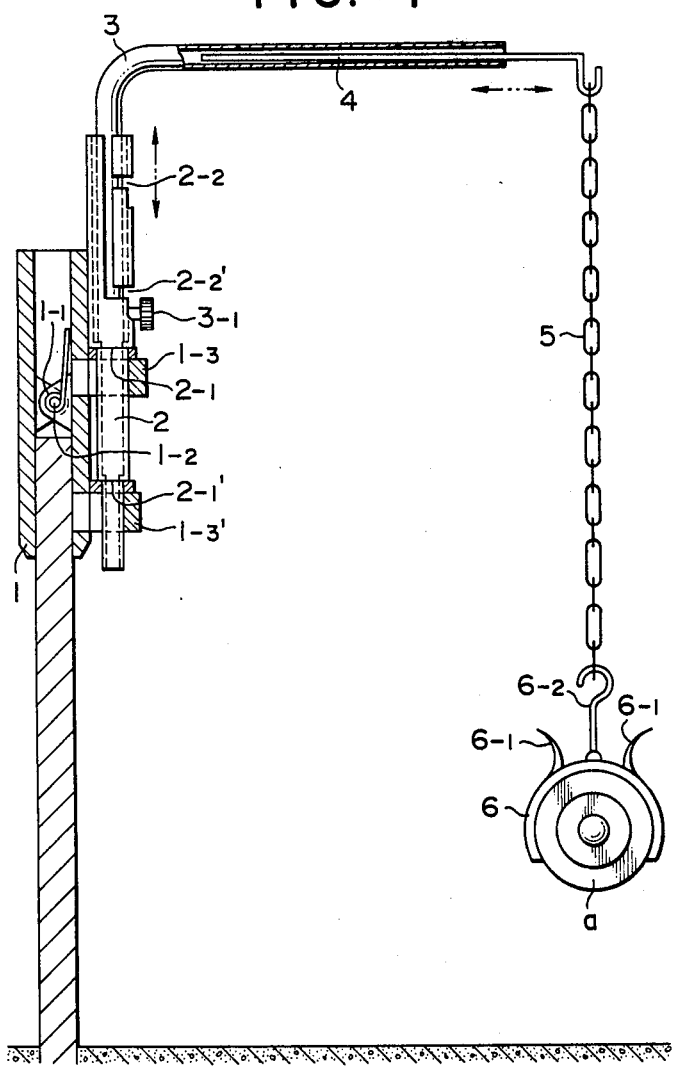
FIG. 1 is a side view of the suspension device with selected portions shown in cross-section.

With particular reference to FIG. 1, spring clamp 1 consists of two plates joined by a clamp pivot rod 1-2. A spring 1—1 is coiled about the clamp pivot rod but has straight sections at both ends which bear on the opposite sides of the clamp to provide the spring bias that enables the clamp to grip the surface to which it is attached.

Figure 2:
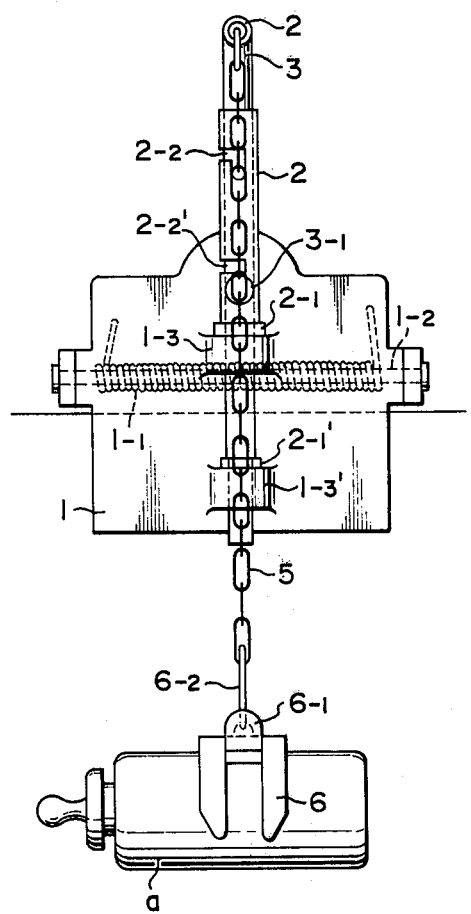
FIG. 2 is an end view of the device shown in FIG. 1.
Figure 3:
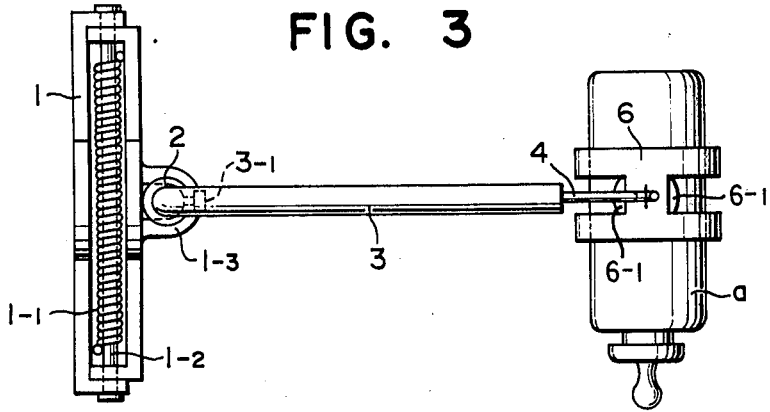
FIG. 3 is a top view of the device shown in FIG. 1.

Tube supports 1-3 and 1-3' are integrally formed with one of the plates of spring clamp 1 as is visible in FIG. 2. These tube supports have holes drilled vertically therethrough to accept vertical support tube 2, and it is noted than the hole in tube support 1-3' is somewhat smaller that the hole in tube support 1-3.

Vertical support tube 2 has two areas of progressively reduced diameter such that the first area fits snuggly within the hole in tube support 1-3 and the second fits snuggly within the hole in tube support 1-3'.

Vertical support tube 2 is hollow to receive L-shaped sleeve 3. The upper portion of vertical support tube 2 has formed therein a plurality of bayonet slots 2-2 and 2-2' which communicate with a vertical slot formed through the wall of the upper portion of support tube 2. This vertical slot and its communicating bayonet slots permit L-shaped sleeve 3 to be locked in positions of varying height by the engagement of detent pin 3-1 with the bayonet slots as best seen in FIG. 2.

An elongated hook 4 is slidably engaged in the horizontal leg of L-shaped sleeve 3 and has formed on one end a hook to engage suspension chain 5.

Nursing bottle a is engaged by bottle clamp 6 which may be formed of a resilient type material to have an inherent spring action. The clamp has two arcuate shaped gripping legs to engage the bottle and two release ears 6-1 to permit disengagement of the bottle by simply pinching the two release ears towards each other. Attached to bottle clamp 6 is a bottle hook 6-2 which is adapted to engage chain 5.

Vertical adjustment of bottle a relative to the surface on which the baby is lying is determined by the location of detent pin 3-1 relative to one of the bayonet slots 2-2, 2-2'. To adjust the height it is merely necessary to grasp L-shaped sleeve 3, lift the same slightly to disengage the detent pin from the bottom of the bayonet slot, rotate the sleeve so that the pin is aligned with the vertical slot in vertical support tube 2, raise the sleeve, and realign it with the upper bayonet slot. A finer degree of adjustment is possible by positioning different links of chain 5 in elongated hook 4. L-shaped sleeve 3 may also be rotated about the longitudinal axis of vertical support tube 2 to facilitate an angular positioning of bottle a. Elongated hook 4 is slidable within hollow L-shaped sleeve 3, thereby permitting a horizontal adjustment of the location of the bottle a. The degree of inclination of bottle a is determined by the location of the center of gravity of the bottle relative to bottle clamp 6. The inclination of bottle a increases as clamp 6 is moved further and further away from the nipple end of bottle a. Spring clamp 1 may be clamped onto any vertical surface such as the side of the crib.

A second preferred embodiment of my invention is best understood with reference to FIGS. 4–6 wherein a vertical support tube 202 is fixedly attached to base plate 201 at one edge thereof, and vertical support rod 203 is positioned within vertical support tube 202. Sufficient clearance is provided between the tube and the rod to permit the rod to be rotated about the longitudinal axis thereof. A generally C-shaped clamping means 205 (see FIG. 6) is adapted to encompass vertical support rod 203 and may be tightened thereon by means of locking pin and thumb screw 204. Horizontal sleeve 209 may be gripped between the facing surfaces of an upturned portion of locking pin 204 and the side of clamp 205 as best visible in FIG. 5. As shown in phantom lines in FIG. 4, horiozontal sleeve 209 may be angularly displaced from the horizontal to facilitate a vertical adjustment of nursing bottle a.

Elongated hook 206 is adapted to slide within horizontal sleeve 209 in a manner similar to that described in the first embodiment disclosed herein. Suspension chain 207 is engaged at its upper end by elongated hook 206 and at the lower end by bottle hook 211 on bottle clamp 208. The bottle clamp is formed from a resilient material and has arcuately shaped portions adapted to engage bottle a, and has release ears 210 that permit disengagement of the bottle in a manner similar to that described with respect to the first embodiment disclosed herein. As is apparent from the phantom line illustration in FIG. 5, the inclination of bottle *a* may be adjusted by positioning clamp 208 relative to the center of gravity of bottle *a*.

The embodiment of FIGS. 4–6 is particularly convenient for those applications where a vertical clamping surface is absent. For example, base plate 201 may be positioned relative to a play mattress positioned on the floor.

Obviously, numerous modifications and variations of the present invention are possible in light of the above teachings. It is therefore to be understood that within the scope of the appended claims the invention may be practiced otherwise than as specifically described herein.

I claim:

1. A device for suspending a nursing bottle from a support member comprising:
    bottle gripping means,
    horizontally adjustable hook means operatively connected to said bottle gripping means, and
    support means, supporting said hook means with means permitting pivotal adjustment of said support means in both a vertical direction and pivotally about a vertical axis, including spring clamp means secured to said support member, tube support means integrally connected to said clamp means, a vertical support tube pivotably disposed within said tube support means and having a plurality of detent engaging means vertically disposed thereon, and an L-shaped sleeve, supporting said hook means, slidably disposed within said vertical support tube and having detent means thereon for selectively engaging said detent engaging means of said vertical support tube.

2. A device for suspending a nursing bottle from a support member, as set forth in claim 1, further comprising:
    said bottle gripping means includes resilient means for supporting said bottle along at least one transverse plane thereof and for permitting said bottle to be longitudinally adjusted with respect to said at least one plane so as to selectively alter the transverse support plane of said gripping means with respect to said bottle; and
    means permitting the freely pivotable suspension of said gripping means upon said hook means depending upon said selected support plane;
    whereby said bottle will be disposed in selectively inclined positions depending upon said selection of said support plane.

3. A device for suspending a nursing bottle from a support member as set forth in claim 1, wherein:
    said tube support means comprise vertically spaced sleeves having means defining vertically extending holes therein of different diameters; and
    said vertical support tube has a stepped configuration, the different diametrical portions thereof being respectively disposed within said tube support sleeve so as to be supported thereby.

* * * * *